United States Patent [19]

Reiter

[11] Plant 4,486

[45] Nov. 20, 1979

[54] RASPBERRY PLANT

[76] Inventor: J. Miles Reiter, 315 Vista Dr., La Selva Beach, Calif. 95076

[21] Appl. No.: 904,151

[22] Filed: May 9, 1978

[51] Int. Cl.[2] ..... A01H 5/00

[52] U.S. Cl. ..... Plt./46

[58] Field of Search ..... Plt./46

*Primary Examiner*—Robert E. Bagwill
*Assistant Examiner*—James R. Feyrer
*Attorney, Agent, or Firm*—Townsend and Townsend

[57] ABSTRACT

A new and distinct red raspberry plant particularly characterized by its everbearing fruit habit by which fruit is borne on primocanes during the first year after planting and on primocanes and floricanes during subsequent years. The plant is also characterized by its thornlessness and high yields. Spring production on floricanes commences about May 10 and peaks during June and early July, about two weeks earlier than Willamette. Fall production peaks during September and early October and production is continuous from May until December. Yields exceed Willamette. The convex cupping of mature leaves is a most distinguishing characteristic of the plant.

4 Drawing Figures

The present invention or discovery relates to a new and distinct variety of red raspberry which was developed from a raspberry breeding and experimentation program begun about 1937 in the Santa Clara Valley by my father, Joseph M. Reiter, berry grower, and Earl V. Goldsmith, plant hybridizer, both now deceased. Breeding ceased in 1953 and the testing and experimentation was abandoned a few years later. Some of the test varieties were maintained, however, in a succession of very small plots.

In spring of 1968, the holding plots which were mixed with a number of experimental varieties were sorted out as to variety and the process of eliminating a number of soil borne diseases was commended. This process extended over a period of years and in 1973, observations disclosed certain desirable and distinct characteristics of the present variety which was asexually reproduced and a testing program established in Watsonville under my supervision.

Through discussions with some of the persons involved in the previous testing program and a review of old notes, it appears that the new variety herein designated "Sweetbriar" was a 1952 cross which at that time was coded 52-37X. Parentage is unascertained.

The accompanying drawings, taken on or about July 20, 1977, show specimens of the "Sweetbriar" variety with fruit and foliage in different stages of development. Grid lines are 5 cm. (approximately 2.5 in.) apart.

FIG. 1 of the accompanying drawing illustrates plant parts of the new variety typical in size and shape, particularly showing the shape of the torus and the well-exposed fruit as well as the irregularity of shape of the drupelets.

Figure 1:
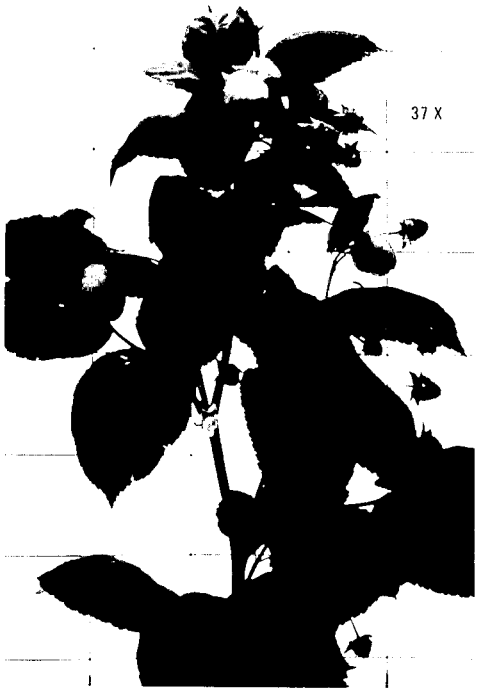
Figure 2:
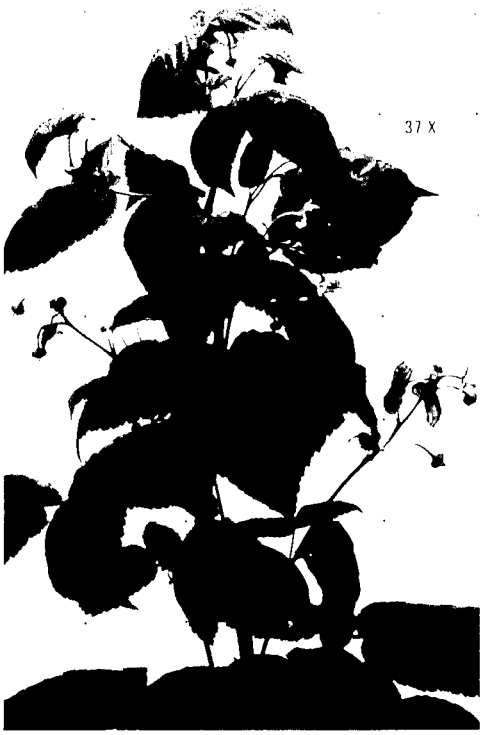
FIG. 2 shows fruit development from inflorescence to green berries and the downward cupping of the leaves better illustrated in FIG. 3.
Figure 3:
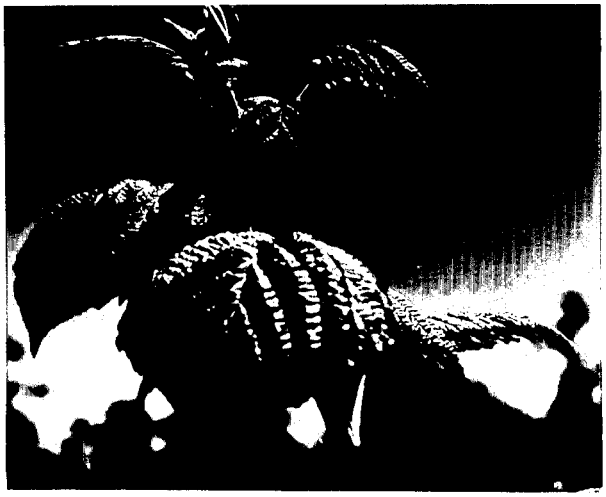
FIG. 3 illustrates the characteristic downward cupping of the leaves, leaf texture and the slight browning of young leaves.
Figure 4:
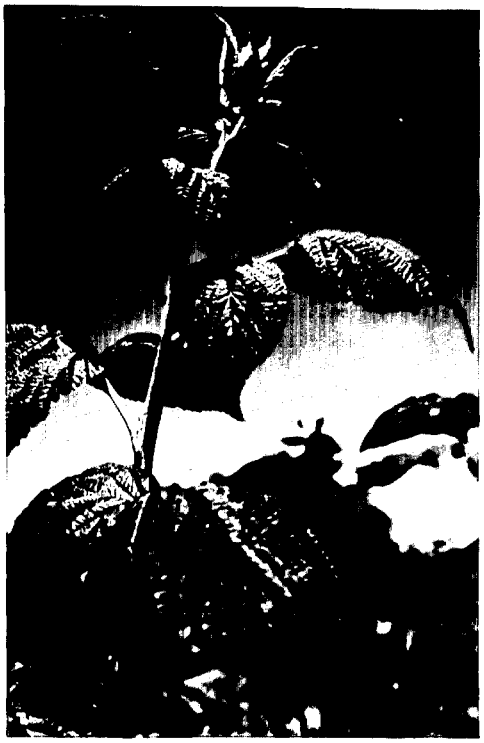
FIG. 4 illustrates a typical primocane of the new variety and the start of inflorescence.

The "Sweetbriar" variety has displayed outstanding novel characteristics such as (1) an everbearing fruiting habit, i.e., fruit is borne on primocanes during the first year after planting and during the second and subsequent years on primocanes and floricanes; (2) thornlessness, i.e., canes lack prickles; and, (3) high yields. On my farm in Watsonville, spring production on floricanes starts approximately May 10 and peaks during the month of June and the first week in July. Fall production on primocanes peaks during September and into early October. The spring crop generally comprises about 35% of the total production and the fall crop 65%. Occasionally, the spring crop will run as high as 50% of the total production. There is some production continuously from May until December. Cropping precedes that of the Willamette variety grown in the same field by approximately two weeks and yields throughout the course of the year exceed those of Willamette.

Plant Description: Terminology used follows that of Asa Gray, Lessons in Botany, revised edition (1901). Everbearer, fruiting on primocanes and floricanes; upright, rigid canes, that are symmetrical from top to bottom reaching an average height by the second year after testing on my Watsonville farm of six to nine feet, which is about two feet shorter than the Willamette variety in the same field. Grown in hedgerows, the "Sweetbriar" variety has flat vertical sides. Primocanes are light green, non-branching and without prickles except for sparse development of soft, light brown prickles at the bases of canes. Floricanes are light brown and branching.

Foliage is mostly three-foliate with occasional five-foliate leaves. The terminal leaflet is cordate and occasionally develops single lobes or one lobe on each side situated approximately midway between the base and the apex. Lobe formation ranges from mere points to independent leaflets.

Mature leaves are deep dull yellow green (1) to dark dull yellow green (see Plate XXXII, Color Standard and Color Nomenclature by Robert Ridgway, Washington, D.C. (1912)), smooth to slightly rugose and cup downward. In immature leaflets, edges are rolled downward parallel to the mid rib to nearly cover the underside of the leaf. This convex cupping of the leaf is one of the most distinguishing characteristics of the "Sweetbriar" variety.

Fruit is borne in raceme clusters, with the terminal cluster bearing eight to twelve berries, and subterminal clusters, typically fewer. Fruit is slightly smaller and firmer than that of the Willamette and larger and softer than that of the Heritage variety. The fruit is rose color to rose red (see Plate XII, Ridgway). The berries are exposed, easy to pick, with the primary berry composed of 75 to 95 drupelets. The fruit is generally conical and symmetrical, however, the individual drupelets tend to be irregular in size.

The receptacle (torus) is cylindrical at its base where sepals and dry stamens remain attached, then tapers to a blunt point.

I claim:

1. The new and distinct variety of raspberry plant herein described and illustrated and identified by the characteristics enumerated above.

* * * * *